US 9,278,093 B2

(12) United States Patent
Ali et al.

(10) Patent No.: US 9,278,093 B2
(45) Date of Patent: Mar. 8, 2016

(54) ALDOSTERONE SYNTHASE INHIBITORS

(71) Applicants: Merck Sharp & Dohme Corp., Rahway, NJ (US); ElexoPharm GmbH, Saarbrucken (DE)

(72) Inventors: Amjad Ali, Freehold, NJ (US); Emmanuel Bey, Forbach (FR); Rolf Hartmann, Saarbrucken (DE); Quingzhong Hu, Saarbrucken (DE); Lina Yin, Saarbrucken (DE)

(73) Assignees: Merck Sharp & Dohme Corp., Rahway, NJ (US); ElexoPharm GmbH, Saarbrucken (DE)

( * ) Notice: Subject to any disclaimer, the term of this patent is extended or adjusted under 35 U.S.C. 154(b) by 0 days.

(21) Appl. No.: 14/389,172

(22) PCT Filed: Mar. 29, 2013

(86) PCT No.: PCT/US2013/034517
§ 371 (c)(1),
(2) Date: Sep. 29, 2014

(87) PCT Pub. No.: WO2013/151876
PCT Pub. Date: Oct. 10, 2013

(65) Prior Publication Data
US 2015/0306091 A1    Oct. 29, 2015

Related U.S. Application Data

(60) Provisional application No. 61/619,958, filed on Apr. 4, 2012.

(51) Int. Cl.
*C07D 471/04*     (2006.01)
*A61K 45/06*      (2006.01)
*A61K 31/4745*    (2006.01)

(52) U.S. Cl.
CPC ............. *A61K 31/4745* (2013.01); *A61K 45/06* (2013.01); *C07D 471/04* (2013.01)

(58) Field of Classification Search
CPC ... C07D 471/04; A61K 31/4145; A61K 45/06
See application file for complete search history.

(56) References Cited

U.S. PATENT DOCUMENTS 9,073,929 B2 *   7/2015   Hoyt et al.

FOREIGN PATENT DOCUMENTS

| WO | WO9532205 A1    | 11/1995 |
| WO | WO9940094 A1    | 8/1999  |
| WO | WO2009135651 A1 | 11/2009 |
| WO | WO2011151411 A1 | 8/2011  |
| WO | WO2012012478 A1 | 1/2012  |
| WO | WO2012148808    | 1/2012  |

OTHER PUBLICATIONS

PreventRetinopathy, 2015, http://www.mayoclinic.org/diseases-conditions/diabetic-retinopathy/basics/prevention/con-20023311.*
PreventKidneyFailure, 2015, http://www.webmd.com/a-to-z-guides/understanding-kidney-disease-prevention.*
PreventHypertension, 2015, http://www.webmd.com/hypertension-high-blood-pressure/guide/preventing-high-blood-pressure.*
Hargovan et al., JRSM Cardiovasc Dis, 2014, http://www.ncbi.nlm.nih.gov/pmc/articles/PMC3930157/.*
Namsolleck et al., Nephrol. Dial. Transplant, 2014, http://ndt.oxfordjournals.org/content/29/suppl_1/i62.full.*
AcuteKidneyFailure, 2015, http://www.mayoclinic.org/diseases-conditions/kidney-failure/basics/prevention/con-20024029.*
Ashwell et al., caplus an 2004:780701 (2004).*
PCT Search Report for International Application No. PCT/US13/34517 mailed on Jul. 5, 2013, 1 page.
Machine Translation of WO1999/040094. Retrieved from EPO.

* cited by examiner

*Primary Examiner* — Sun Jae Yoo
(74) *Attorney, Agent, or Firm* — Janet E. Fair; Anna L. Cocuzzo

(57) ABSTRACT

This invention relates to tricyclic triazole compounds or their pharmaceutically acceptable salts. The inventive compounds selectively inhibit aldosterone synthetase. This invention also provides for pharmaceutical compositions comprising the above-cited compounds or their salts as well as potentially to methods for the treatment, amelioration or prevention of conditions that could be treated by inhibiting aldosterone synthetase.

-continued
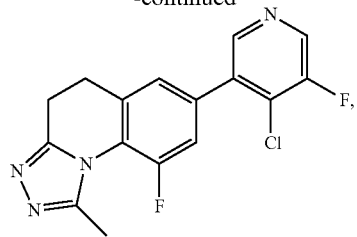
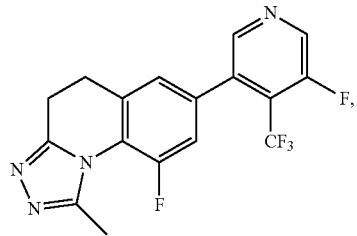
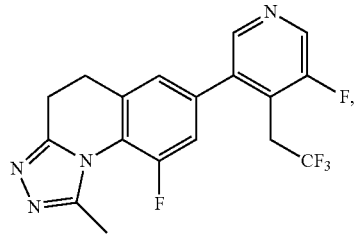
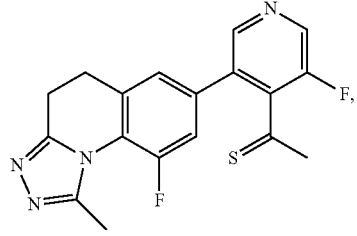
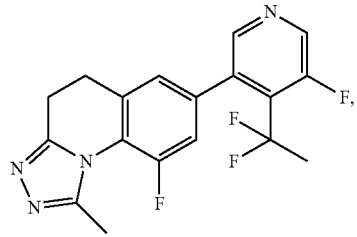
-continued
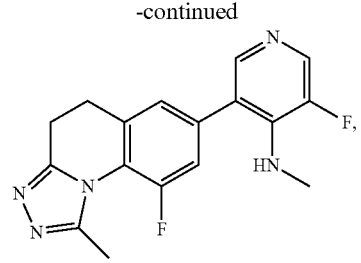
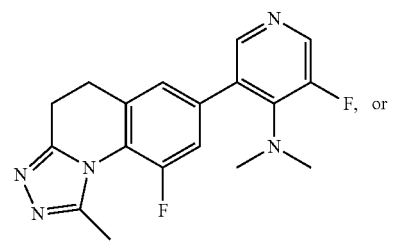
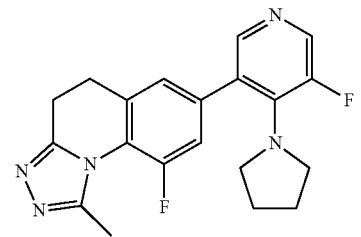
9 Claims, No Drawings

ALDOSTERONE SYNTHASE INHIBITORS

RELATED APPLICATIONS

This application claims benefit to U.S. provisional application Ser. No. 61/619,958, filed Apr. 4, 2012, herein incorporated by reference.

FIELD OF THE INVENTION

The present invention relates to specific tricyclic triazole compounds, which selectively inhibit aldosterone synthetase (CYP11B2) with diminished inhibition or affect on steroid-11-β-hydroxylase (CYP11B1) inhibitors. The inventive compounds potentially have utility in treating cardiovascular diseases such as hypertension or heart failure. The present invention also relates to pharmaceutical compositions comprising the inventive compounds as well as processes for their preparation.

BACKGROUND OF THE INVENTION

Aldosterone is a steroid hormone secreted in the adrenal cortex. In primary cells of the distal tubules and collecting ducts of the kidney, aldosterone binding to the mineralocorticoid receptor (MR) results in the retention of sodium and water and excretion of potassium, which in turn leads to increased blood pressure. Aldosterone also causes inflammation that leads to fibrosis and remodeling in the heart, vasculature and kidney. This inflammation may proceed by MR-dependent as well as MR-independent mechanisms (Gilbert, K. C. et al., Curr. Opin. Endocrinol. Diabetes Obes., vol. 17, 2010, pp. 199-204).

Mineralocorticoid receptor antagonists (MRAs), such as spironolactone and eplerenone, have been used previously to block the effects of aldosterone binding to MR. When given in addition to standard therapies such as angiotensin-converting enzyme (ACE) inhibitors and loop diuretics, the nonselective MRA spironolactone and the selective MRA eplerenone significantly reduced morbidity and mortality in patients with heart failure or myocardial infarction (Pitt, B. et al., New Engl. J. Med., vol. 341, 1999, pp. 709-717; Pitt, B. et al., New Engl. J. Med., vol. 348, 2003, pp. 1382-1390). However, the nonselective MRA spironolactone can also bind to and act at other steroid receptors, and as a consequence its use is associated with sexual side effects such as gynecomastia, dysmenorrhoea and impotence (Pitt, B. et al., New Engl. J. Med., vol. 341, 1999, pp. 709-717; MacFadyen, R. J. et al., Cardiovasc. Res., vol. 35, 1997, pp 30-34; Soberman, J. E. et al., Curr. Hypertens. Rep., vol. 2, 2000, pp 451-456). Additionally, both spironolactone and eplerenone are known to cause elevated plasma postassium levels (hyperkalemia) and elevated aldosterone levels.

An alternative method of blocking the effects of aldosterone is to inhibit its biosynthesis. CYP11B2 is a mitochondrial cytochrome P450 enzyme that catalyzes the final oxidative steps in the conversion of 11-deoxycorticosterone, a steroidal precursor, to aldosterone (Kawamoto, T. et al., Proc. Natl. Acad. Sci. USA, vol. 89, 1992, pp. 1458-1462). Compounds that inhibit CYP11B2 should thus inhibit the formation of aldosterone. Such compounds, particularly those of nonsteroidal structure, should provide the beneficial effects of MRAs, without the adverse effects derived from steroid receptor binding or MR-independent inflammatory pathways.

CYP11B1 is a related enzyme that catalyzes the formation of glucocorticoids, such as cortisol, an important regulator of glucose metabolism. Because human CYP11B2 and CYP11B1 are greater than 93% homologous, it is possible for nonselective compounds to inhibit both enzymes (Kawamoto, T. et al., Proc. Natl. Acad. Sci. USA, vol. 89, 1992, pp 1458-1462; Taymans, S. E. et al., J. Clin. Endocrinol. Metab., vol. 83, 1998, pp 1033-1036). It would be preferable, however, for therapeutic agents to selectively inhibit CYP11B2 and the formation of aldosterone with diminished inhibition of, or affect on, CYP11B1 and the production of cortisol.

WO 2009/135651 to Elexopharm describes 6-pyridin-3yl-3,4,-dihydro-1H-quinolin-2-one derivatives as being CYP11B2 inhibitors. Two compounds described therein are lactam derivatives of the formula:

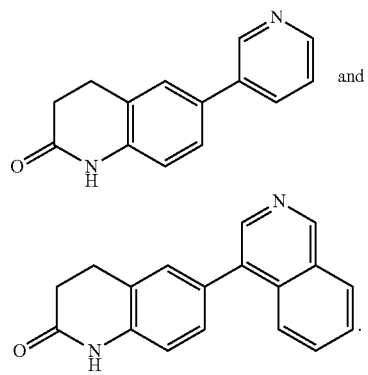

Structurally similar lactam and thiolactam compounds are disclosed by Lucas et al., J. Med. Chem. 2008, 51, 8077-8087; those compounds are said to be potential inhibitors of CYP11B2. Lucas et al. in J. Med. Chem. 2011, 54, 2307-2309 describes certain pyridine substituted 3,4-dihydro-1H-quinolin-2-ones as being highly potent as selective inhibitors of CYP11B2 and WO 2012/012478 to Merck describes benzimidazole analogues as having the ability to CYP11B2. An abstract of a dissertation reports that a series of novel heterocyclic-substituted 4,5-dihydro-[1,2,4]triazolo[4,3a]quinolones was evaluated for its aldosterone synthase activity; one of the compounds is reported as exhibiting excellent selectivity of CYP11B2 over CYP11B1. WO 2012/148808 to Merck and ElexoPharm also discloses tricyclic triazole compounds that possess aldosterone synthase activity.

WO 1999/40094 to Bayer AG describes oxazolidinone derivatives with azol-containing tricycles as possessing antimicrobial activity. An example of one of the compounds disclosed therein is:

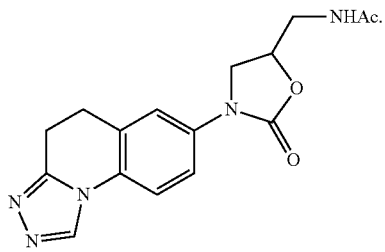 [SMILES: CC(=O)NCC1CN(c2ccc3c(c2)CCc2nncn2-3)C(=O)O1]

The compounds of the invention provide an alternative to previous treatments for elevated aldosterone levels and inhibit CYP11B2.

SUMMARY OF THE INVENTION

In it many embodiments, the present invention provides for specific tricyclic triazole compounds ("compounds of the invention") selected from the following group of compounds:

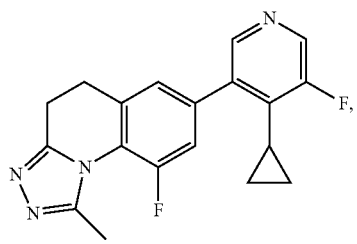

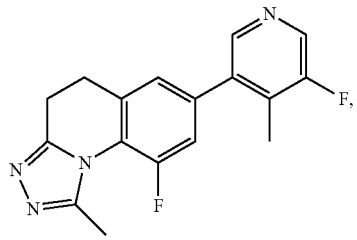

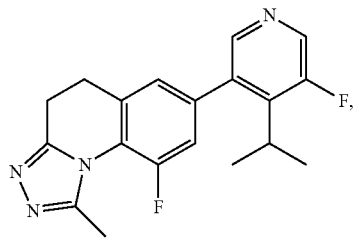

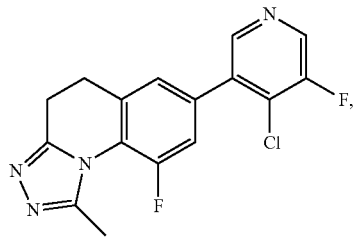

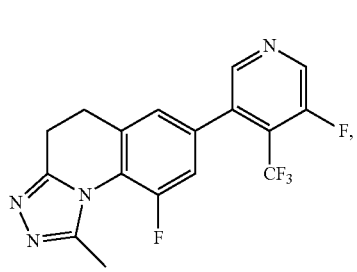

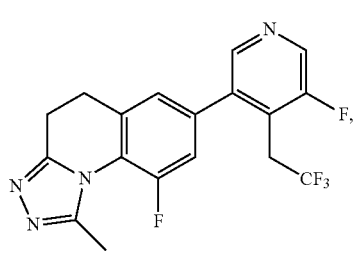

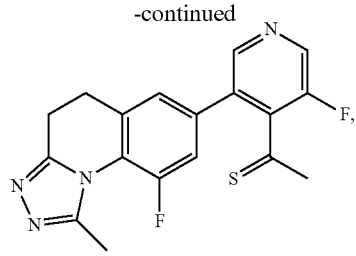

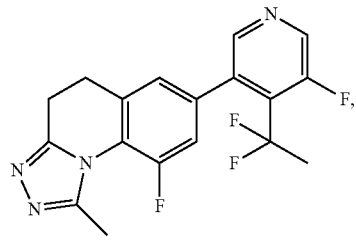

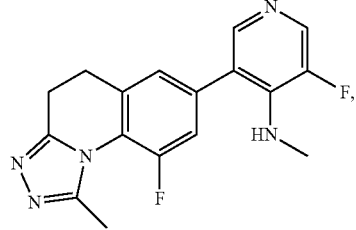

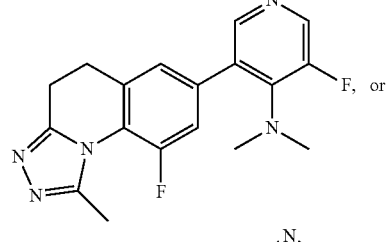

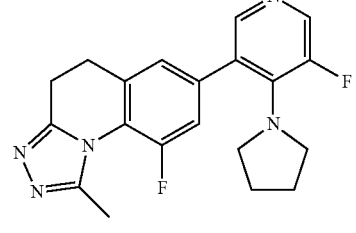

or a pharmaceutically acceptable salt thereof, which are inhibitors of CYP11B2, or metabolites, stereoisomers, salts, solvates or polymorphs thereof, processes of preparing such compounds, pharmaceutical compositions comprising one or more such compounds, processes of preparing pharmaceutical compositions comprising one or more such compounds and potentially to methods of treatment, prevention, inhibition or amelioration of one or more disease states associated with inhibiting CYP11B2 by administering an effective amount at least one of the compounds of the invention to a patient in need thereof.

Another aspect of the present invention is pharmaceutical compositions comprising a therapeutically effective amount of at least one compound of the compounds of the invention or a pharmaceutically acceptable salt thereof and a pharmaceutically acceptable carrier.

Another aspect of the present invention is pharmaceutical compositions comprising a therapeutically effective amount of at least one compound of the compounds of the invention or a pharmaceutically acceptable salt thereof, a therapeutically effective amount of at least one additional therapuetic agent and a pharmaceutically acceptable carrier.

It is further contemplated that the combination of the invention could be provided as a kit comprising in a single package at least one compound of the invention or a pharmaceutically acceptable salt thereof in a pharmaceutical composition, and at least one separate pharmaceutical composition, such as, for example a separate pharmaceutical composition comprising a therapeutic agent.

The compounds of the present invention could be useful in the treatment, amelioration or prevention of one or more conditions associated with inhibiting CYP11B2 by administering a therapeutically effective amount of at least one compound of the invention or a pharmaceutically acceptable salt thereof to a mammal in need of such treatment. Conditions that could be treated or prevented by inhibiting CYP11B2 include hypertension, heart failure, such as congestive heart failure, diastolic dysfunction, left ventricular diastolic dysfunction, diastolic heart failure, systolic dysfunction, hypokalemia, renal failure, in particular chronic renal failure, restenosis, metabolic syndrome, nephropathy, post-myocardial infarction, coronary heart diseases, increased formation of collagen, fibrosis and remodeling following hypertension and endothelial dysfunction, cardiovascular diseases, renal dysfunction, liver diseases, vascular diseases, cerebrovascular diseases, retinopathy, neuropathy, insulinopathy, endothelial dysfunction, ischemia, myocardial and vascular fibrosis, myocardial necrotic lesions, vascular damage, myocardial infarction, left ventricular hypertrophy, cardiac lesions, vascular wall hypertrophy, endothelial thickening or fibrinoid necrosis of coronary arteries.

Another embodiment of the present invention is the use of a compound of the invention or a pharmaceutically acceptable salt thereof for the manufacture of a medicament for the treatment, amelioration or prevention of one or more conditions associated with inhibiting CYP11B2 in a patient.

DETAILED DESCRIPTION

As used above, and throughout this disclosure, the following terms, unless otherwise indicated, shall be understood to have the following meanings:

"Patient" includes both human and animals.

"Mammal" means humans and other mammalian animals.

The present invention encompasses all stereoisomeric forms of the compounds of the invention. Centers of asymmetry that may be present in the compounds of the invention can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism, the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of the invention or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

Reference to the compounds of this invention as those of a specific formula specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the claimed compounds For example, different isotopic forms of hydrogen (H) include protium ($^1$H) and deuterium ($^2$H). Protium is the predominant hydrogen isotope found in nature.

Enriching for deuterium may afford certain therapeutic advantages, such as increasing in vivo half-life or reducing dosage requirements, or may provide a compound useful as a standard for characterization of biological samples. Isotopically-enriched compounds of the present invention can be prepared without undue experimentation by conventional techniques well known to those skilled in the art or by processes analogous to those described in the Examples herein using appropriate isotopically-enriched reagents and/or intermediates.

When the compounds of the invention contain one or more acidic or basic groups the invention also includes the corresponding physiologically or toxicologically acceptable salts, in particular the pharmaceutically utilizable salts. Thus, the compounds of the invention that contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of the invention that contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. I Salts can be obtained from the compounds of the invention by customary methods which are known to the person skilled in the art, for example by combination with an organic or inorganic acid or base in a solvent or dispersant, or by anion exchange or cation exchange from other salts. The present invention also includes all salts of the compounds the invention that, owing to low physiological compatibility, are not directly suitable for use in pharmaceuticals but which can be used, for example, as intermediates for chemical reactions or for the preparation of physiologically (i.e., pharmaceutically) acceptable salts.

Furthermore, compounds of the present invention might exist in amorphous form and/or one or more crystalline forms, and as such all amorphous and crystalline forms and mixtures thereof of the compounds of the invention are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Accordingly, the specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Compounds of the present invention are effective at inhibiting the synthesis of aldosterone by inhibiting CYP11B2 (aldosterone synthase) and they may be therefore useful agents for the therapy and prophylaxis of disorders that are associated with elevated aldosterone levels. Accordingly, an object of the instant invention is to provide a method for inhibiting aldosterone synthase, and more particularly selectively inhibiting CYP11B2, in a patient in need thereof, comprising administering a compound of Formula I to the patient in an amount effective to inhibit aldosterone synthesis, or more particularly to selectively inhibit CYP11B2, in the patient. A selective inhibitor of CYP11B2 is intended to mean a compound that preferentially inhibits CYP11B2 as compared to CYP11B1. The inhibition of CYP11B2, as well inhibition of CYP11B1, by the compounds of the invention can be examined, for example, in the inhibition assay described below. Another object is to provide selective inhibitors for CYP11B2 that are potent.

In general, compounds that have activity as aldosterone synthase inhibitors can be identified as those compounds which have an $IC_{50}$ of less than or equal to about 10 μM; preferably less than or equal to about 250 nM; and most preferably less than or equal to about 100 nM, in the V79-Human-CYP11B2 Assay described below. In general, aldosterone synthase inhibitors that are selective for inhibition of CYP11B2 as compared to CYP11B1 are those that show at least 3-fold greater inhibition for CYP11B2 compared to CYP11B1; preferably at least 20-fold inhibition for CYP11B2 compared to CYP11B1; and more preferably at least 100-fold greater inhibition for CYP11B2 compared to CYP11B1, in the V79-Human-CYP11B2 Assay as compared to the V79-Human-CYP11B1 Assay.

Due to their ability to inhibit CYP11B2, the compounds of the present invention may be useful to treat and/or ameliorate the risk for hypertension, hypokalemia, renal failure (e.g., chronic renal failure), restenosis, Syndrome X, nephropathy, post-myocardial infarction, coronary heart diseases, increased formation of collagen, fibrosis and remodeling following hypertension and endothelial dysfunction, cardiovascular diseases, renal dysfunction, liver diseases, vascular diseases, cerebrovascular diseases, retinopathy, neuropathy, insulinopathy, endothelial dysfunction, heart failure (e.g., congestive heart failure), diastolic heart failure, left ventricle diastolic dysfunction, diastolic heart failure, systolic dysfunction, ischemia, myocardial and vascular fibrosis, myocardial necrotic lesions, vascular damage, myocardial infarction, left ventricular hypertrophy, cardiac lesions, vascular wall hypertrophy, endothelial thickening or necrosis of coronary arteries.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of the invention. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 30 mg/kg, preferably 0.001 to 20 mg/kg, in particular 0.01 to 10 mg/kg (in each case mg per kg of bodyweight) is appropriate for administration to an adult weighing approximately 75 kg in order to obtain the desired results. The daily dose is preferably administered in a single dose or, in particular when larger amounts are administered, can be divided into several, for example two, three or four individual doses, and may be, for example but not limited to, 0.1 mg, 0.25 mg, 0.5 mg, 0.75 mg, 1 mg, 1.25 mg, 2.5 mg, 5 mg, 10 mg, 20 mg, 40 mg, 50 mg, 75 mg, 100 mg, etc., on a daily basis. In some cases, depending on the individual response, it may be necessary to deviate upwards or downwards from the given daily dose.

Administering of the drug to the patient includes both self-administration and administration to the patient by another person. The patient may be in need of treatment for an existing disease or medical condition, or may desire prophylactic treatment to prevent or reduce the risk of said disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention of myocardial infarction.

In the methods of treatment of this invention, the compound may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred, particularly solid oral dosage units such as pills, tablets or capsules.

Accordingly, this invention also provides pharmaceutical compositions comprised of a compound of the invention and a pharmaceutically acceptable carrier. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. Pharmaceutical compositions may also contain other customary additives, for example, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of the invention with a pharmaceutically acceptable carrier. Also encompassed is the pharmaceutical composition which is made by combining a compound of the invention with a pharmaceutically acceptable carrier. The carrier is comprised of one or more pharmaceutically acceptable excipients. Furthermore, a therapeutically effective amount of a compound of this invention can be used for the preparation of a medicament useful for inhibiting aldosterone synthase, inhibiting CYP11B2, for normalizing a disturbed aldosterone balance, or for treating or preventing any of the medical conditions described herein, in dosage amounts described herein.

The amount of active compound of the invention and its pharmaceutically acceptable salts in the pharmaceutical composition may be, for example but not limited to, from 0.1 to 200 mg, preferably from 0.1 to 50 mg, per dose on a free acid/free base weight basis, but depending on the type of the pharmaceutical composition and potency of the active ingredient it could also be lower or higher. Pharmaceutical compositions usually comprise 0.5 to 90 percent by weight of the active compound on a free acid/free base weight basis.

Since the compounds of the invention inhibit aldosterone synthase, apart from use as pharmaceutically active compounds in human medicine and veterinary medicine, they can also be employed as a scientific tool or as aid for biochemical investigations in which such an effect on aldosterone synthase and aldosterone levels is intended, and also for diagnostic purposes, for example in the in vitro diagnosis of cell samples or tissue samples. The compounds of the invention can also be employed as intermediates for the preparation of other pharmaceutically active compounds.

One or more additional pharmacologically active agents (or therapeutic agents) may be administered in combination with a compound of the invention. An additional active agent (or agents) is intended to mean a pharmaceutically active agent (or agents) different from the compound of the invention. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme (ACE) inhibitors (e.g, alacepril, benazepril, captopril, ceronapril, cilazapril, delapril, enalapril, enalaprilat, fosinopril, imidapril, lisinopril, moexepril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists (e.g., eprosartan, irbesartan, losartan, olmesartan, telmisartan, valsartan) neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, bepridil, diltiazem, felodipine, gallopamil, nicardipine, nifedipine, niludipine, nimodipine, nisoldipine veraparmil), potassium channel activators (e.g., nicorandil, pinacidil, cromakalim, minoxidil, aprilkalim, loprazolam), diuretics (e.g., hydrochlorothiazide) including loop diuretics such as ethacrynic acid, furosemide, bumetanide and torsemide, sympatholitics, beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, pravastatin, atorvastatin rosuvastatin, ezetimibe); niacin in immediate-release or controlled release forms, and particularly in niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds (e.g., muraglitazar, glipizide, stigliptin, metformin, rosiglitazone); or with other drugs beneficial for the prevention or the treatment of the above-mentioned diseases including nitroprusside and diazoxide.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods and one skilled in the art would have resources such as *Chemical Abstracts* or *Beilstein* at his or her disposal to assist in devising an alternative method of preparing a specific compound.

The compounds of the present invention can be prepared according to the procedures of the following Schemes using appropriate materials and are further exemplified by the specific Examples which follow. Moreover, by utilizing the procedures described herein, one of ordinary skill in the art can readily prepare additional compounds of the present invention claimed herein.

Throughout the synthetic schemes, abbreviations are used with the following meanings unless otherwise indicated:

BuLi, n-BuLi=n-butyllithium; Celite®=diatomaceous earth; conc, conc.=concentrated; DME=dimethylether; DMEM=Dulbecco's modified eagle medium; DMF=N,N-dimethylformamide; DMSO=dimethylsulfoxide; eq.=equivalent(s); h, hr=hour; HPLC=high pressure liquid chromatography; Lawesson's Reagent=2,4-bis(4-methoxyphenyl)-1,3,2,4-dithiadiphosphetane 2,4-disulfide; LCMS=liquid chromatography-mass spectroscopy; MS=mass spectroscopy; min, min.=minute; NBS=N-bromosuccinimide; NMR=nuclear magnetic resonance; r.t.=room temperature; sat.=saturated; THF=tetrahydrofuran and V=volume.

As will be known to those skilled in the art, in all schemes, the compounds of the invention and all synthetic intermediates may be purified from unwanted side products, reagents and solvents by recrystallization, trituration, preparative thin layer chomatography, flash chomatography on silica gel as described by W. C. Still et al, J. Org. Chem. 1978, 43, 2923, or reverse-phase HPLC. Compounds purified by HPLC may be isolated as the corresponding salt.

Additionally, in some instances the final compounds of Formula I and synthetic intermediates may be comprised of a mixture of cis and trans isomers, enantiomers or diastereomers. As will be known to those skilled in the art, such cis and trans isomers, enantiomers and diastereomers may be separated by various methods including crystallization, chomatography using a homochiral stationary phase and, in the case of cis/trans isomers and diastereomers, normal-phase and reverse-phase chomatography.

Chemical reactions were monitored by LCMS, and the purity and identity of the reaction products were assayed by LCMS (electrospray ionization) and NMR. Data for $^1$H NMR are reported with chemical shift (δ ppm), multiplicity (s=singlet, d=doublet, t=triplet, q=quartet, m=multiplet, br s=broad singlet, br m=broad multiplet), coupling constant (Hz), and integration. Unless otherwise noted, all LCMS ions listed are [M+H]. All temperatures are degrees Celsius unless otherwise noted.

EXAMPLE 1

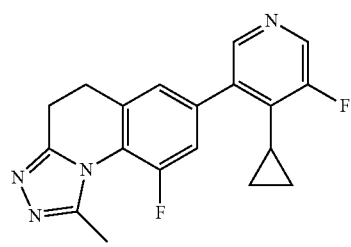 [SMILES: Cc1nnc2n1-c1c(F)cc(-c3cncc(F)c3C3CC3)cc1CC2]

7-(4-cyclopropyl-5-fluoropyridin-3-yl)-9-fluoro-1-methyl-4,5-dihydro-[1,2,4]triazolo[4,3-a]quinoline

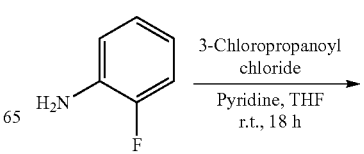

-continued

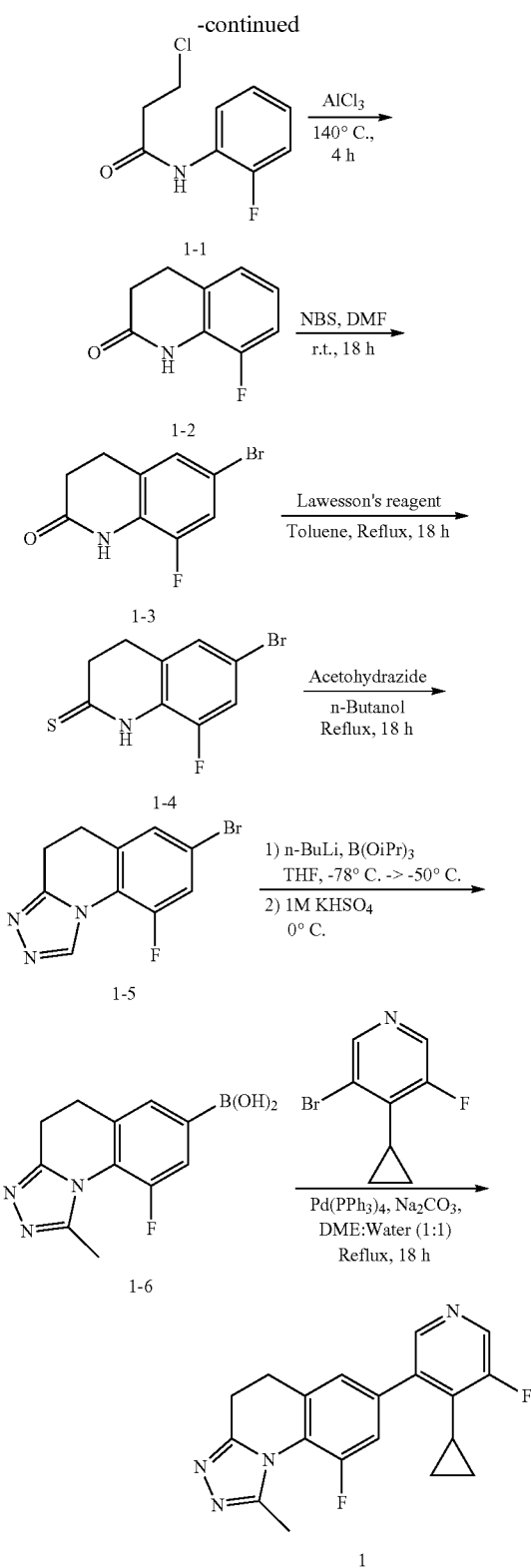

Step A. 3-chloro-N-(2-fluorophenyl)propanamide

A solution of 2-fluoroaniline (20.00 g, 180.0 mmol) in tetrahydrofurane (100 mL) and pyridine (22 mL) was stirred for 15 min and then 3-chloropropionyl chloride (25.14 g, 198 mmol) in tetrahydrofurane (50 ml) was added at 0° C. The mixture was stirred for 18 h at room temperature under inert atmosphere. After the completion of the reaction, the mixture was diluted with water. The aqueous layer was separated and extracted with diethylether. The collected organic parts were washed with water and brine and were then dried over $Na_2SO_4$, filtered and concentrated under vacuum to afford the title compound as a white solid. This intermediate was used directly in the next step without further purification and characterization.

Step B. 8-fluoro-3,4-dihydroquinolin-2(1H)-one

A mixture of 3-chloro-N-(2-fluorophenyl)propanamide (1-1, 17.2 g, 85.30 mmol) and aluminium trichloride (56.9 g, 427.0 mmol) was heated at 140° C. for 4 h under inert atmosphere. After cooling the reaction mixture down to 0° C., ice cold water (350 mL) was added slowly. The resulting precipitate was collected by filtration and washed with water and hexane. The crude compound was purified by flash chromatography on silica gel to obtain the title compound as a white solid. This intermediate was used directly in the next step without characterization.

Step C. 6-bromo-8-fluoro-3,4-dihydroquinolin-2(1H)-one

To a stirred solution of 8-fluoro-3,4-dihydroquinolin-2(1H)-one (1-2; 8.30 g, 50.10 mmol) in N,N-dimethylformamide (250 mL) was added N-bromosuccinimide (9.80 g, 55.10 mmol) in N,N-dimethylformamide (120 mL) at 0° C. The reaction mixture was stirred at room temperature for 18 h, cooled, and diluted with ice cold water (500 mL). The resulting precipitated was filtered and dried to obtain the title compound as a white solid; $^1$H NMR (DMSO-$D_6$, 500 MHz) δ=10.20 (s, 1H), 7.37 (dd, J=2.0 Hz, $J_{HF}$=10.0 Hz, 1H), 7.26 (s, 1H), 2.93 (t, J=7.0 Hz, 2H), 2.47 (t, J=7.5 Hz, 2H).

Step D. 6-bromo-8-fluoro-3,4-dihydroquinoline-2(1H)-thione

To a suspension of 6-bromo-8-fluoro-3,4-dihydroquinolin-2(1H)-one (1-3, 2.00 g, 8.19 mmol) in toluene (50 mL) was added Lawesson's reagent (1.66 g, 4.10 mmol). After refluxing the reaction mixture for 2 h, the toluene was distilled off to yield the crude product, which was then purified by flash chromatography on silica gel to obtain the title compound as a yellow solid; $^1$H NMR (DMSO-$D_6$, 500 MHz) δ=12.14 (s, 1H), 7.46 (dd, J=2.0 Hz, $J_{HF}$=10.0 Hz, 1H), 7.34 (s, 1H), 2.94 (d, J=8.0 Hz, 2H), 2.84 (d, J=8.0 Hz, 2H).

Step E. 7-Bromo-9-fluoro-4,5-dihydro-1-methyl-[1,2,4]triazolo[4,3-a]quinoline A suspension of 6-bromo-8-fluoro-3,4-dihydroquinoline-2(1H)-thione (1-4, 1.71 g, 6.57 mmol) and acetohydrazide (0.58 g, 7.89 mmol) in n-butanol (7 mL) was refluxed for 18 h under inert atmosphere. After cooling down to ambient temperature, ethyl acetate (10 mL) and water (10 mL) were added. The organic phase was then separated and the water phase was extracted with ethyl acetate (5×10 mL). The combined organic phases were washed with brine and dried over $Na_2SO_4$; the combined organic layers were then evaporated under reduced pressure to yield the crude product. The crude compound was purified by flash chromatography on silica gel to obtain the title compound as a white solid; $^1$H NMR (DMSO-D$_6$, 500 MHz) δ=7.79 (dd, J=2.0 Hz, J$_{HF}$=11.0 Hz, 1H), 7.63 (s, 1H), 2.95 (br s, 4H), 2.46 (d, J$_{HF}$=8.5 Hz, 3H).

Step F. (9-Fluoro-1-methyl-4,5-dihydro-[1,2,4]triazolo[4,3-a]quinolin-7-yl)boronic acid 7-Bromo-9-fluoro-4,5-dihydro-1-methyl[1,2,4]triazolo[4,3-a]quinoline (1-5, 3.90 g, 13.8 mmol) was dissolved under nitrogen atmosphere in dry THF and cooled to −78° C. A 2.5 M n-BuLi solution in hexane (V=6.60 ml, 16.6 mmol) was added dropwise and stirred at −78° C. for 30 min. Triisopropyl borate (V=4.5 ml, 19.3 mmol) was added in one portion and the temperature raised to −50° C. for additional 30 min. The mixture was allowed to warm up to 0° C. and quenched with a 1M KHSO$_4$ solution in order to reach pH 3. The solution was basified with a 2M NaOH solution and washed twice with ethyl acetate. The water layer was neutralized with conc. HCl and the precipitate was successively washed with water and ether and dried under reduced pressure to obtain the title compound as a white solid; MS (ESI): m/z=248.04 [M+H]$^+$.

Step G. 7-(4-Cyclopropyl-5-fluoropyridin-3-yl)-9-fluoro-1-methyl-4,5-dihydro-[1,2,4]triazolo[4,3-a]quinoline 3-Bromo-4-cyclopropyl-5-fluoropyridine (462 mg, 2.14 mmol) was dissolved in a mixture of DME (3.55 mL) and water (3.55 mL). Sodium carbonate (226 mg, 2.14 mmol), (9-fluoro-1-methyl-4,5-dihydro-[1,2,4]triazolo[4,3-a]quinolin-7-yl)boronic acid (1-6, 176 mg, 0.71 mmol) and tetrakis triphenylphosphine palladium catalyst (4.11 mg, 3.6 mop were added. The mixture was deoxygenated under reduced pressure, flushed with nitrogen and heated under reflux for 18 h. After cooling to room temperature, ethyl acetate (10 mL) and water (10 mL) were added and the organic layer was separated. The water phase was extracted with ethyl acetate (2×10 mL). The combined organic phases were washed with brine, dried over Na$_2$SO$_4$, filtered over a short plug of Celite® and evaporated under reduced pressure. The crude compound was purified using preparative thin layer chromatography (ethyl acetate/ethanol 6:4) in order to yield the title compound as a white solid; $^1$H NMR (CD$_3$SOCD$_3$, 500 MHz) δ 8.49 (d, J=2.5 Hz, 1H), 8.35 (s, 1H), 7.60 (dd, J=1.8, 12.0 Hz, 1H), 7.52 (d, J=1.8 Hz, 1H), 3.80 (br. s, 4H), 2.54-2.52 (m, 3H), 1.96-1.95 (m, 1H), 0.89-0.87 (m, 2H), 0.68-0.67 (m, 2H); MS (ESI): m/z=338.97 [M+H]$^+$.

The compounds in Table 1 were prepared using chemistry described in Example 1.

TABLE 1

| Example | Structure | IUPAC Name | LCMS |
|---|---|---|---|
| 2 | 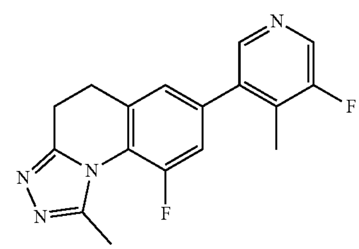 [SMILES: Cc1c(F)cncc1-c1cc(F)c2c(c1)CCc1nnc(C)n1-2] | 9-fluoro-7-(5-fluoro-4-methylpyridin-3-yl)-1-methyl-4,5-dihydro-[1,2,4]triazolo[4,3-a]quinoline | 313.04 |
| 3 | 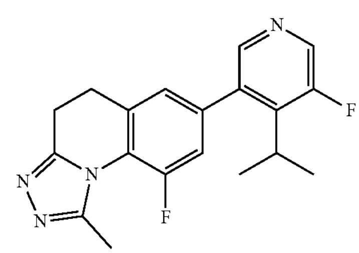 [SMILES: Cc1nnc2n1-c1c(F)cc(-c3cncc(F)c3C(C)C)cc1CC2] | 9-fluoro-7-(5-fluoro-4-isopropylpyridin-3-yl)-1-methyl-4,5-dihydro-[1,2,4]triazolo[4,3-a]quinoline | 341.02 |
| 4 | 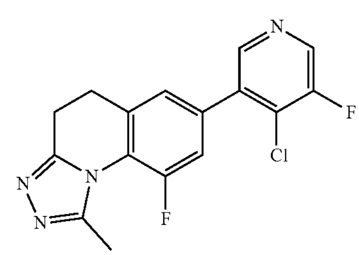 | 7-(4-chloro-5-fluoropyridin-3-yl)-9-fluoro-1-methyl-4,5-dihydro-[1,2,4]triazolo[4,3-a]quinoline | 332.93 |

The compounds in Table 2 are prepared using chemistry described in Example 1.

TABLE 2

| Example | Structure | IUPAC Name |
| --- | --- | --- |
| 5 | 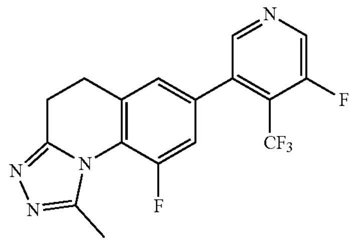 | 9-fluoro-7-(5-fluoro-4-(trifluoromethyl)pyridin-3-yl)-1-methyl-4,5-dihydro-[1,2,4]triazolo[4,3-a]quinoline |
| 6 | 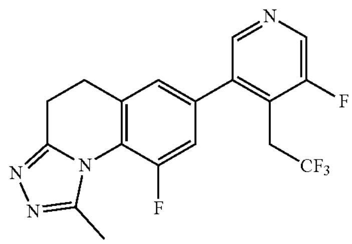 [SMILES: Cc1nnc2n1-c1c(F)cc(-c3cncc(F)c3CC(F)(F)F)cc1CC2] | 9-fluoro-7-(5-fluoro-4-(2,2,2-trifluoroethyl)pyridin-3-yl)-1-methyl-4,5-dihydro-[1,2,4]triazolo[4,3-a]quinolin |
| 7 | 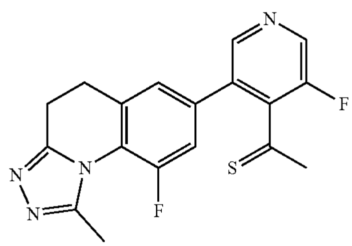 [SMILES: CC(=S)c1c(F)cncc1-c1cc(F)c2c(c1)CCc1nnc(C)n1-2] | 1-(3-fluoro-5-(9-fluoro-1-methyl-4,5-dihydro-[1,2,4]triazolo[4,3-a]quinolin-7-yl)pyridin-4-yl)ethanethione |
| 8 | 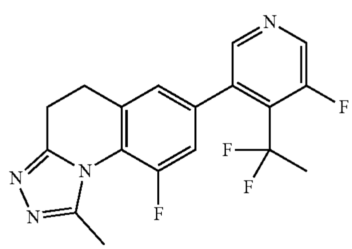 [SMILES: Cc1nnc2n1-c1c(F)cc(-c3cncc(F)c3C(C)(F)F)cc1CC2] | 7-(4-(1,1-difluoroethyl)-5-fluoropyridin-3-yl)-9-fluoro-1-methyl-4,5-dihydro-[1,2,4]triazolo[4,3-a]quinoline |
| 9 | 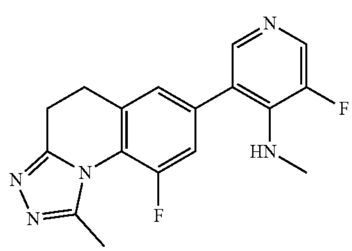 [SMILES: CNc1c(F)cncc1-c1cc(F)c2c(c1)CCc1nnc(C)n1-2] | 3-fluoro-5-(9-fluoro-1-methyl-4,5-dihydro-[1,2,4]triazolo[4,3-a]quinolin-7-yl)-N-methylpyridin-4-amine |
| 10 | 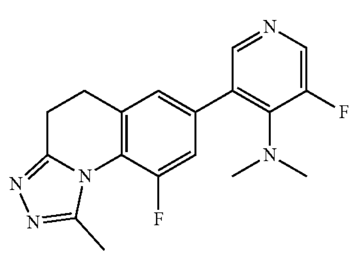 | 3-fluoro-5-(9-fluoro-1-methyl-4,5-dihydro-[1,2,4]triazolo[4,3-a]quinolin-7-yl)-N,N-dimethylpyridin-4-amine |

TABLE 2-continued

| Example | Structure | IUPAC Name |
|---|---|---|
| 11 | 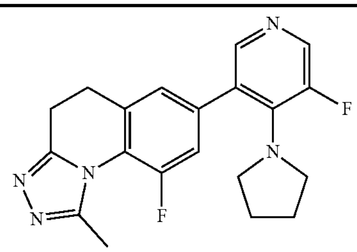 | 9-fluoro-7-(5-fluoro-4-(pyrrolidin-1-yl)pyridin-3-yl)-1-methyl-4,5-dihydro-[1,2,4]triazolo[4,3-a]quinoline |

Assay Description:

Compounds of the Examples 1 to 3 were assayed for V79-Human-CYP11B2 and V79-Human-CYP11B1 by modifying the protocol described in *J. Steroid Biochem. Mol. Biol.* 81; 173-179 (2002). V79MZh11B1 and V79MZh11B2 cells ($8 \times 10^5$ cells/well) were grown on 24-well culture plates until confluence. Before testing, the DMEM culture medium was removed and 450 µl of fresh DMEM containing the inhibitor was added to each well. After a preincubation step of 60 min at 37° C., the reaction was started by the addition of 50 µl of DMEM in which the substrate deoxycorticosterone (containing 0.15 µCi of [1,2-3H]-deoxycorticosterone in ethanol, final test concentration 100 nM) was dissolved. Incubation times were 25 min for V79MZh11B1 and 50 min for V79MZh11B2 cells at 37° C., respectively. The enzyme reactions were stopped by extracting the supernatant with ethyl acetate. Samples were centrifuged (10.000 g, 5 min) and the solvent was pipetted into fresh cups. After evaporation of the solvent, the steroids were redissolved in 40 µl of methanol (50:50, v/v) and analyzed by HPLC. Detection and quantification of the steroids were performed using a radioflow detector. To first estimate the different $IC_{50}$ values, five different concentrations ranging from 1 to 10.000 nM were measured. For the following $IC_{50}$ determination, three different concentrations (repeat-determinations) were measured for each $10_{50}$ value of each inhibitor in which the second concentration led to an inhibition of approximately 40 to 60%. The inhibitor concentrations were all in the linear range of the dose-response-curves, so that the coefficients of correlation were at least 0.95 for each determination. The final $IC_{50}$ value was estimated as the average of three or four independent $IC_{50}$ values and a selectivity factor corresponding to the ratio between the $10_{50}$ values of CYP11B1 and CYP11B2 was calculated for each substance.

TABLE 3

| Example | Structure | IUPAC Name | V79 human CYP11B2 $IC_{50}$ nM | V79 human CYP11B1 $IC_{50}$ nM |
|---|---|---|---|---|
| 1 | 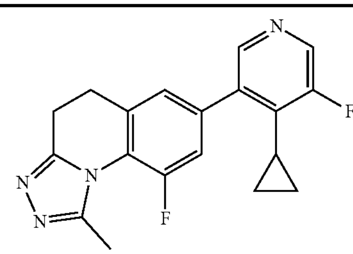 | 7-(4-cyclopropyl-5-fluoropyridin-3-yl)-9-fluoro-1-methyl-4,5-dihydro-[1,2,4]triazolo[4,3-a]quinoline. | 7.3 | 2293 |
| 2 | 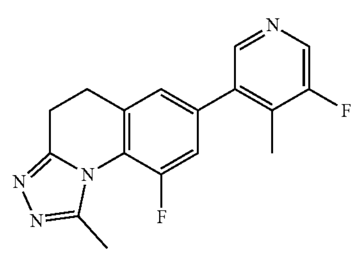 [SMILES: Cc1c(F)cncc1-c1cc(F)c2c(c1)CCc1nnc(C)n1-2] | 9-fluoro-7-(5-fluoro-4-methylpyridin-3-yl)-1-methyl-4,5-dihydro-[1,2,4]triazolo[4,3-a]quinoline | 6.0 | 1424 |
| 3 | 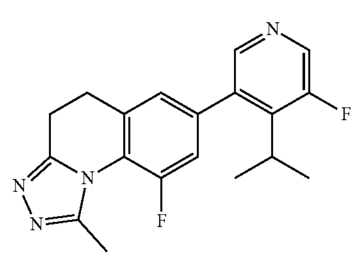 [SMILES: Cc1nnc2n1-c1c(F)cc(-c3cncc(F)c3C(C)C)cc1CC2] | 9-fluoro-7-(5-fluoro-4-isopropylpyridin-3-yl)-1-methyl-4,5-dihydro-[1,2,4]triazolo[4,3-a]quinoline | 9.5 | 3971 |

TABLE 3-continued

| Example | Structure | IUPAC Name | V79 human CYP11B2 IC$_{50}$ nM | V79 human CYP11B1 IC$_{50}$ nM |
|---|---|---|---|---|
| 4 | 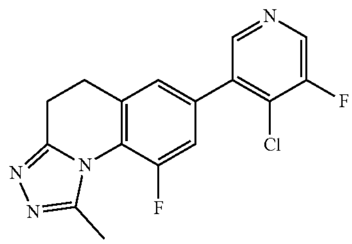 [SMILES: Cc1nnc2n1-c1c(F)cc(-c3cncc(F)c3Cl)cc1CC2] | 7-(4-chloro-5-fluoropyridin-3-yl)-9-fluoro-1-methyl-4,5-dihydro-[1,2,4]triazolo[4,3-a]quinoline | 21.6 | 9802 |

While the invention has been described with reference to certain particular embodiment thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

We claim:

1. A compound of the formula:

-continued

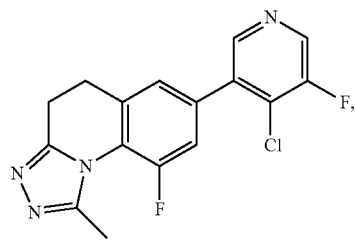

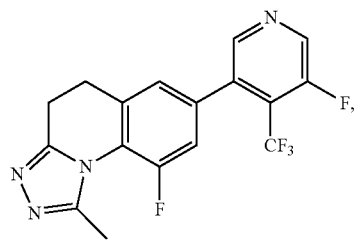

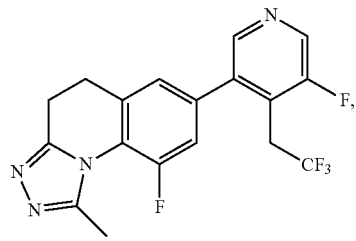

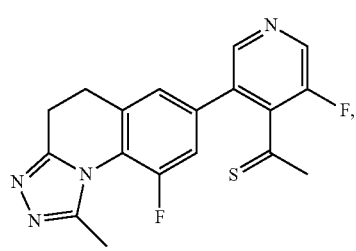

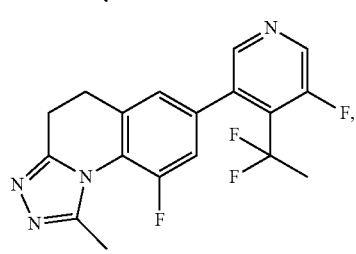

-continued

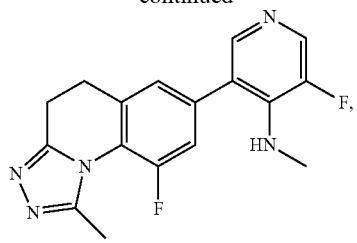

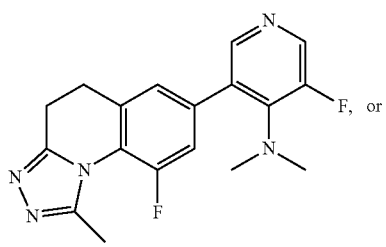

or a pharmaceutically acceptable salt thereof.

2. The compound of claim 1 which is

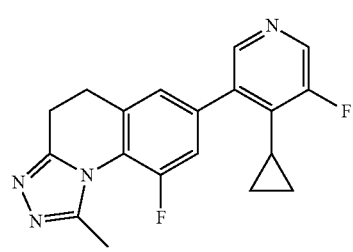

or a pharmaceutically acceptable salt thereof.

3. The compound of claim 1 which is

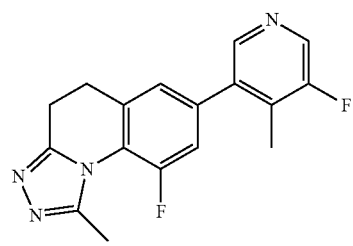

or a pharmaceutically acceptable salt thereof.

4. The compound of claim 1 which is

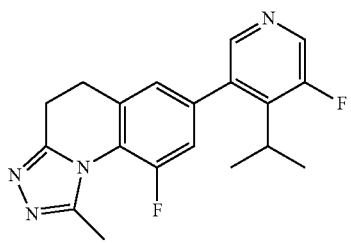 [SMILES: Cc1nnc2n1-c1c(F)cc(-c3cncc(F)c3C(C)C)cc1CC2]

or a pharmaceutically acceptable salt thereof.

5. The compound of claim 1 which is

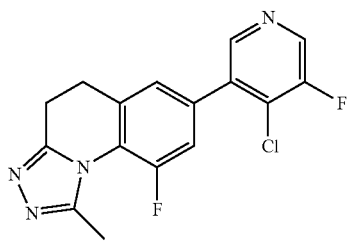 [SMILES: Cc1nnc2n1-c1c(F)cc(-c3cncc(F)c3Cl)cc1CC2]

or a pharmaceutically acceptable salt thereof.

6. A pharmaceutical composition comprising a therapeutically effective amount of at least one compound as defined in claim 1 or a pharmaceutically acceptable salt thereof and a pharmaceutically acceptable carrier.

7. A pharmaceutical composition comprising a therapeutically effective amount of at least one compound as defined in claim 1 or a pharmaceutically acceptable salt thereof, a therapeutically effective amount of at least one additional therapuetic agent and a pharmaceutically acceptable carrier.

8. A method for the treatment or amelioration of one or more of the conditions associated with inhibiting CYP11B2, which comprises administering therapeutically effective amount of at least one compound as defined in claim 1 or a pharmaceutically acceptable salt thereof to mammal in need of such treatment, wherein the conditions that could be treated or ameliorated by inhibiting CYP11B2 are hypertension, left ventricular diastolic dysfunction, renal failure, retinopathy.

9. A method for inhibiting CYP11B2 in a mammal in need thereof which comprises administering to said mammal an effective amount of a compound of the formula:

-continued
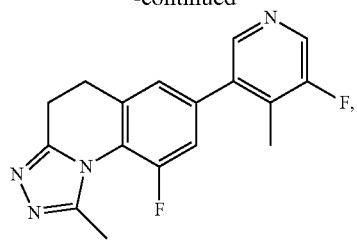
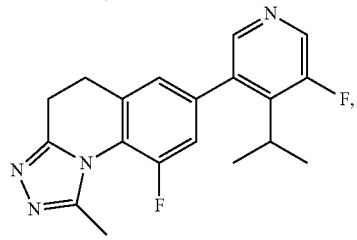
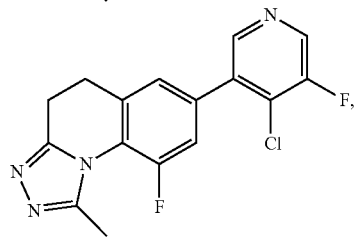
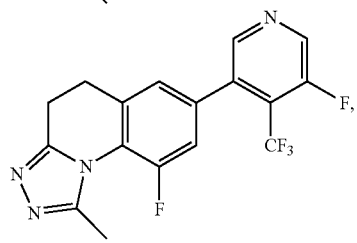
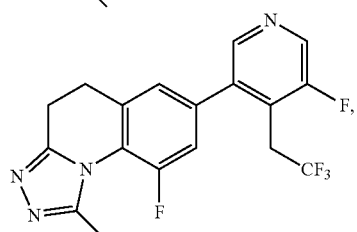
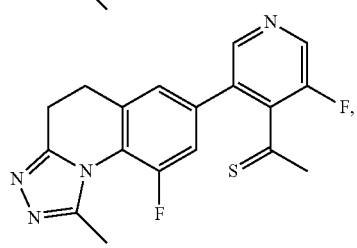
-continued
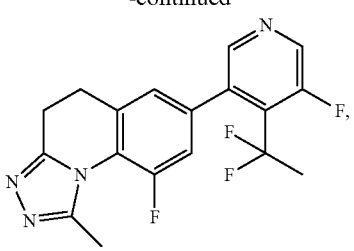
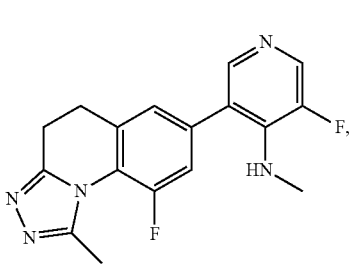
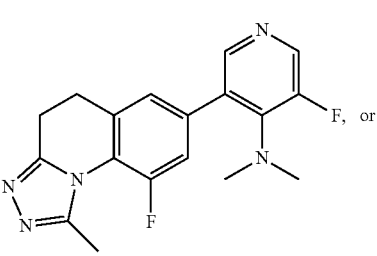, or
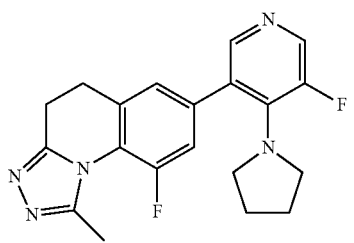
or a pharmaceutically acceptable salt thereof.
* * * * *